United States Patent [19]

Ono et al.

[11] Patent Number: 5,032,836
[45] Date of Patent: Jul. 16, 1991

[54] GUIDING DEVICE FOR VISUALLY HANDICAPPED PERSON

[75] Inventors: Yujiro Ono, Tokyo; Syuichi Nakatome, Kawasaki; Yoshihide Kumada, Tokyo; Kenji Suzuki, Odawara; Junichi Kawamura, Yokohama; Katunori Ota, Akishima; Satoru Tomiyama, Koganei, all of Japan

[73] Assignee: Namco, Ltd., Tokyo, Japan

[21] Appl. No.: 541,180

[22] Filed: Jun. 18, 1990

Related U.S. Application Data

[63] Continuation of Ser. No. 300,628, Jan. 23, 1989, abandoned.

[30] Foreign Application Priority Data

Jan. 27, 1988 [JP] Japan ............................. 63-8120[U]
Oct. 20, 1988 [JP] Japan ........................... 63-136136[U]

[51] Int. Cl.⁵ ............................................ G08C 19/00
[52] U.S. Cl. .............................. 340/825.710; 320/49; 340/825.690; 340/825.720

[58] Field of Search ................. 340/825.69, 825.71, 340/825.72, 825.36, 825.17, 571, 572, 539; 331/63, 64; 455/226, 343; 180/167, 168; 320/49; 342/24

[56] References Cited

U.S. PATENT DOCUMENTS

| | | | |
|---|---|---|---|
| 3,225,265 | 12/1965 | Krause et al. | 340/825.72 X |
| 3,550,105 | 12/1970 | DeCola et al. | 331/64 X |
| 3,795,896 | 3/1974 | Isaacs | 340/825.36 |
| 4,191,948 | 3/1980 | Stockdale | 340/539 |
| 4,232,308 | 11/1980 | Lee et al. | 340/539 |
| 4,591,835 | 5/1986 | Sharp | 340/571 X |
| 4,804,943 | 2/1989 | Soleimani | 340/571 X |

FOREIGN PATENT DOCUMENTS

| | | | |
|---|---|---|---|
| 0172985 | 7/1988 | Japan | 340/825.72 |
| 2074816 | 11/1981 | United Kingdom | 340/825.72 |

*Primary Examiner*—Ulysses Weldon
*Attorney, Agent, or Firm*—Jordan and Hamburg

[57] ABSTRACT

A guide device for visually handicapped person which has a portable unit and a position indicator unit. The portable unit is carried by the visually handicapped person and includes a radio frequency signal oscillator. The position indicator unit is disposed to a desired place and includes a radio frequency signal receiver and a loud speaker.

3 Claims, 9 Drawing Sheets

GUIDING DEVICE FOR VISUALLY HANDICAPPED PERSON

This application is a continuation of application Ser. No. 300,628, filed Jan. 23, 1989, now abandoned.

BACKGROUND OF THE INVENTION

The present invention relates to a guiding device for guiding a visually handicapped person to an aimed place.

For a visually handicapped person in a hotel room or in a train, it may be relatively easy to get closer to an aimed place by means of estimated course, distance thereto and atomosphere, etc. Even so, however, it may be difficult to get the aimed place exactly.

OBJECTS OF THE INVENTION

An object of the present invention is to provide a guiding device capable of guiding a visually handicapped person to an aimed place exactly and of being used by him easily regardless of location of the aimed place.

Another object of the present invention is to provide such device as mentioned above, which is capable of informing a consumption of battery used as a power source of the device.

SUMMARY OF THE INVENTION

The guiding device for visually handicapped person, according to the present invention, includes a portable unit and a position indicator unit. The portable unit is equipped with a radio frequency (RF) signal transmitter for transmitting a RF signal. The portable unit is carried by the visually handicapped person, say, in his pocket or his hand. The position indicator unit includes a RF receiver for receiving the RF signal transmitted by the portable unit and a loud speaker responsive to the received RF signal for generating audible signal. The position indicator unit is adapted to be disposed at an aimed place such as door of a hotel room and a seat in a train to which the visually handicapped person is about to get.

As mentioned previously, it is relatively easy for the visually handicapped person to get closer to the aimed place. When he gets closer to the place, the RF signal transmitted from the portable unit is received by the receiver of the position indicator unit disposed at the aimed place and an audio signal is generated by the loud speaker. He can get the aimed place exactly by means of the audio signal.

DESCRIPTION OF THE PREFERRED EMBODIMENTS

Figure 1:
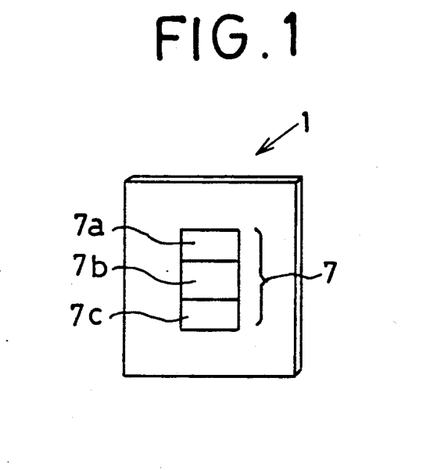
FIG. 1 is a perspective view of an example of a portable unit.
Figure 2:
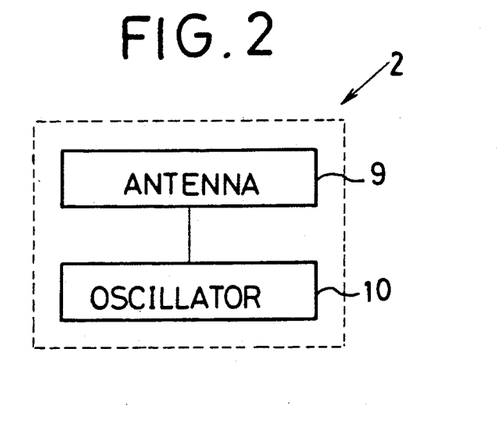
FIG. 2 is a block circuit diagram of an example of a RF signal transmitter.

FIG. 1 shows a portable unit 1. The portable unit 1 includes a RF signal transmitter 2 composed of an antenna 9 and an oscillator 10 as shown in FIG. 2. The RF signal transmitter 2 has an output power small enough to cover a distance as short as about 10 meters, for example. Such transmitter can be constituted with any conventional circuit and, due to its compactness, it is possible to make the portable unit 1 compact and light weight, which is desired since it has to be always carried by a visually handicapped person.

Figure 3:
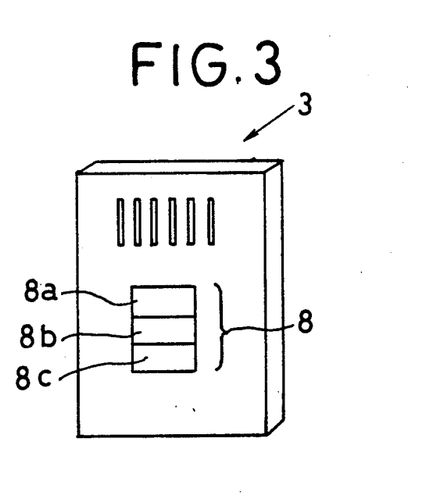
FIG. 3 is a perspective view of an example of a position indicator unit.
Figure 4:
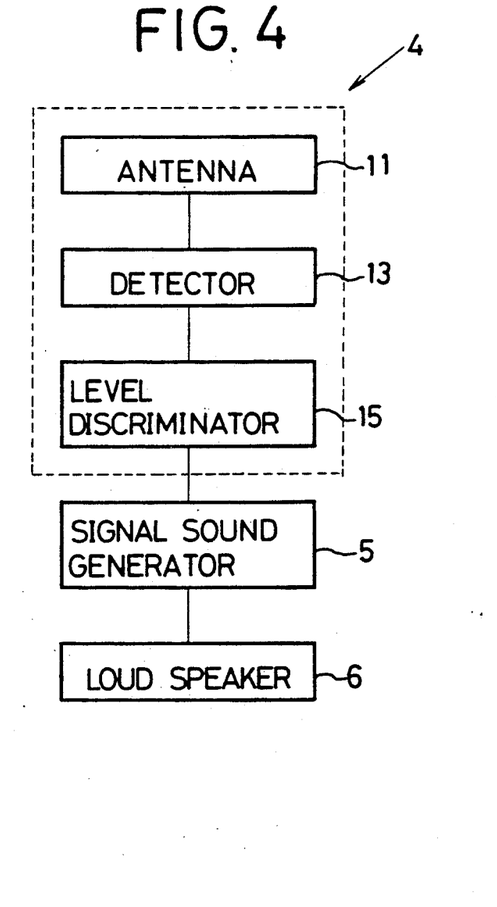
FIG. 4 is a block circuit diagram of an exmaple of a RF signal receiver.

FIG. 3 shows a position indicator unit 3 which includes a RF signal receiver 4, an audio signal generator 5 and a loud speaker 6 as shown in FIG. 4. The RF signal receiver 4 is composed of an antenna 11, a detector 13 and a level discriminator 15. A RF signal transmitted by the RF signal transmitter 2 shown in FIG. 2 is selectively received by the RF signal receiver 4 and discriminated in level. When the level exceeds a predetermined reference level, the loud speaker 6 is driven by the audio signal generator 5 to produce suitable sound. That is, the audio signal generator 5 is a drive circuit responsive to an output of the level discriminator 15 for driving the loud speaker 6. The position indicator unit 3 is set or mounted at a place such as entrance of a building, public telephone, train seat, class room seat, etc., which is the place aimed by the visually handicapped person. It may be possible to mount such position indicator unit even on his white stick so that, when he drops it, he can pick it up easily.

Parts depicted by 7 in FIG. 1 and 8 in FIG. 3 are sets of switches. The switch set 7 includes three switches 7a, 7b and 7c and the set 8 includes three switches 8a, 8b and 8c. In each switch set, one of the three switches is a power switch and the remaining two switches are used to switch a transmission frequency of the RF signal transmitter 2 or a receiving signal frequency of the RF receiver 4 between two values. A first one of the two frequency values is common for the portable units 1 and, if a suitable one of the switches of the switch set 8 of the position indicator unit 3 disposed at, for example, an entrance of a conference room has been depressed, all of the persons who carry the respective portable units 1 are informed by sound generated by the position indicator unit 3 when they approach the conference room.

The other, second frequency value is common for specific one of the portable units 1 and specific one of the position indicator units 3, so that, when one of the switches of the switch set 7 of one of the portable units 1 and one of the switches of the switch set 8 of the position indicator unit 3 have been depressed to select the second frequency and when the portable unit 3 approaches the position indicator unit 3, the latter generates sound. The position indicator unit 3 does not produce such sound when other portable units than the specific unit approach it. Such specific frequency is used only between the specific portable unit and the specific position indicator unit.

When a position indicator unit 3 which is set to the first frequency is disposed at any public facility such as library, etc., any person who carry his own portable unit 1 can be guided thereto by setting its frequency to the first frequency.

Although, in the above embodiment, each unit has selectable two frequencies for common use and private use, it is clear that a single frequency can be used to cover all of the units.

Figure 5:
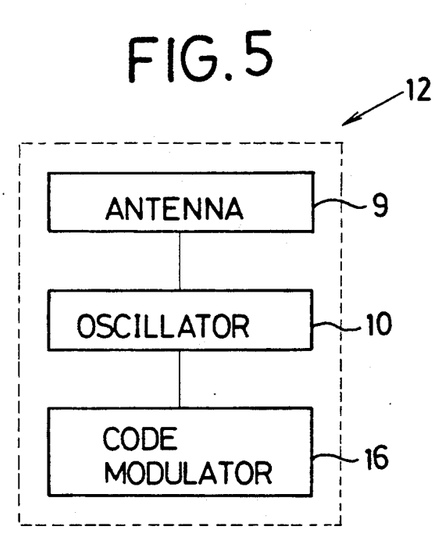
FIG. 5 is a block circuit diagram of another example of the RF signal transmitter.
Figure 6:
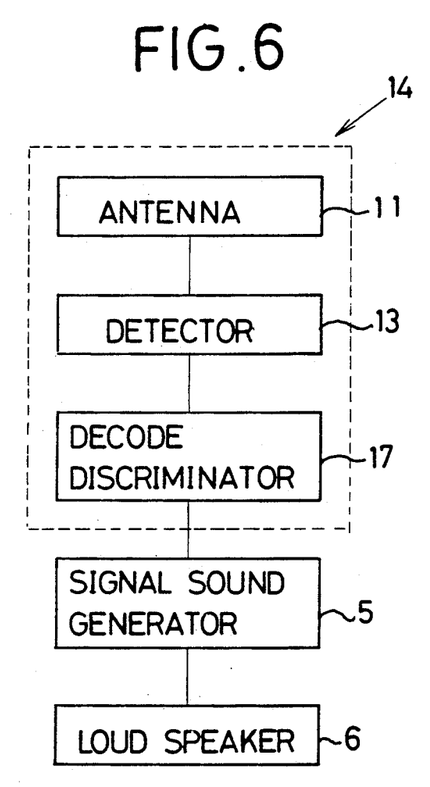
FIG. 6 is a block circuit diagram of another example of the RF receiver.

Further, it is possible to provide in the RF signal transmitter 12 a code modulator 16 as shown in FIG. 5 so that a specific code signal which may be defined by a specific frequency or amplitude and assigned to a different portable unit 3 is generated. In such case, such specific code signal is received by the RF signal receiver 14 having a decoder/discriminator portion 17 as shown in FIG. 6. The effect of this modification is substantially the same as that described before.

Figure 7:
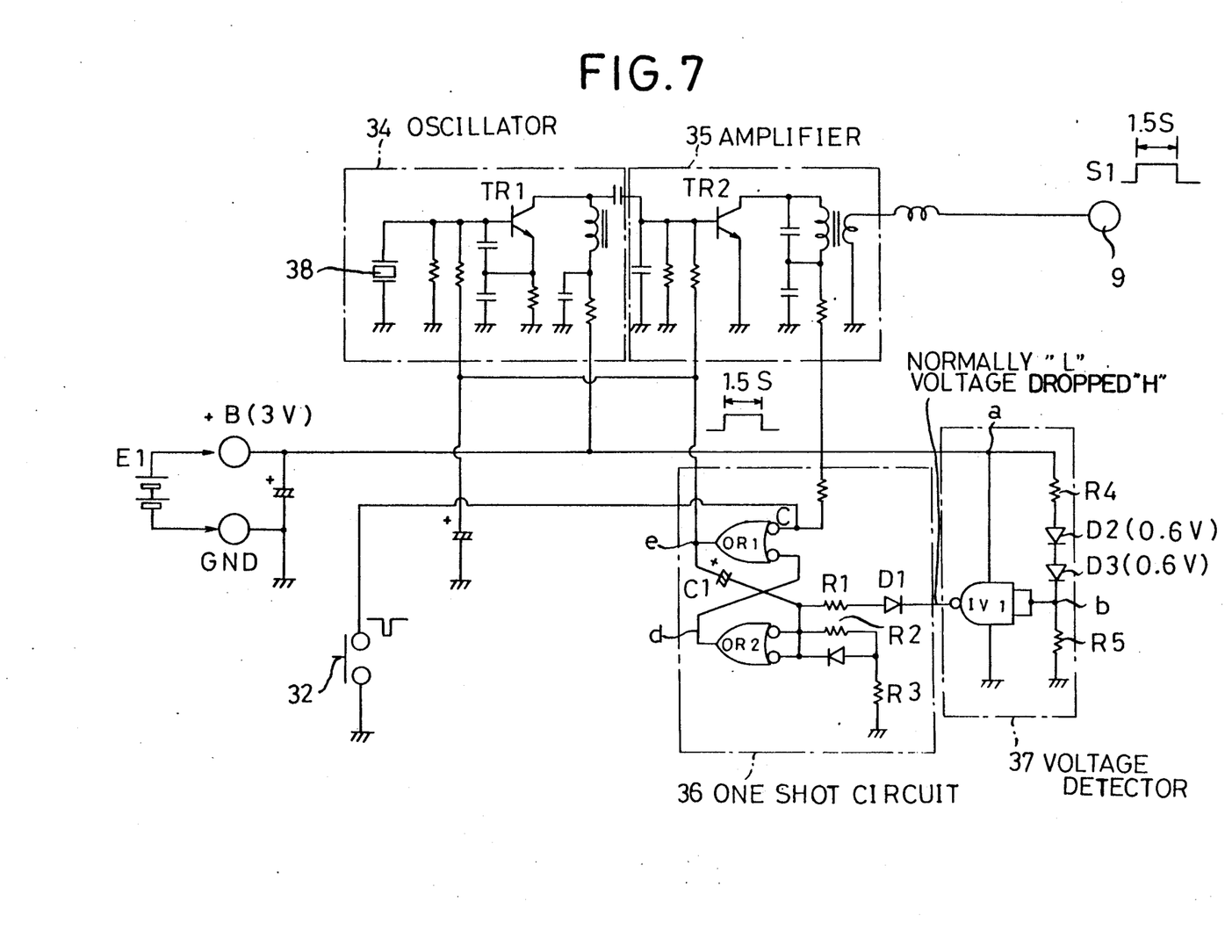
FIG. 7 is a circuit diagram of the RF signal transmitter.
Figure 8:
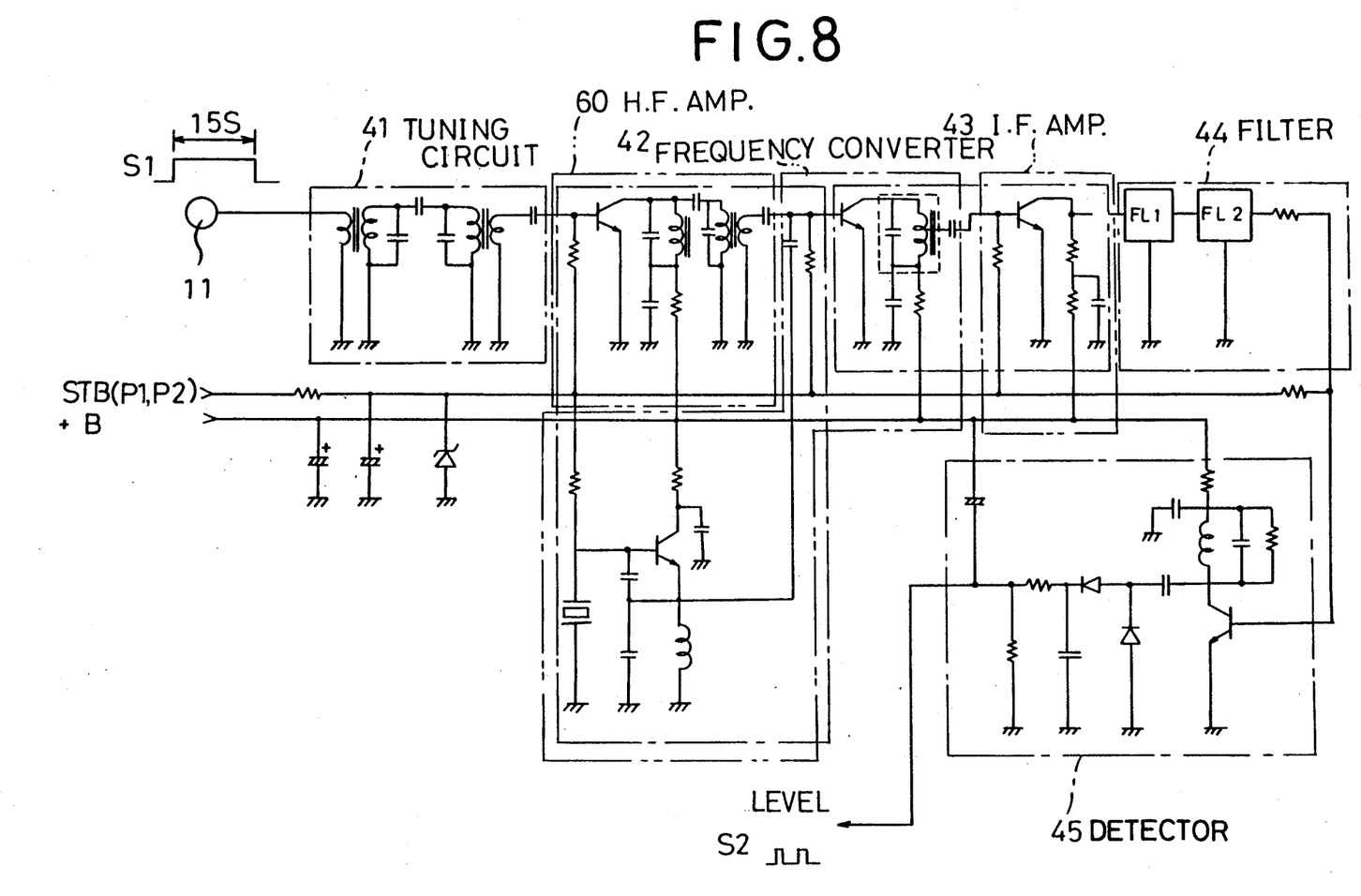
FIGS. 8 and 9 are circuit diagrams of the RF signal receivers, respectively.
Figure 9:
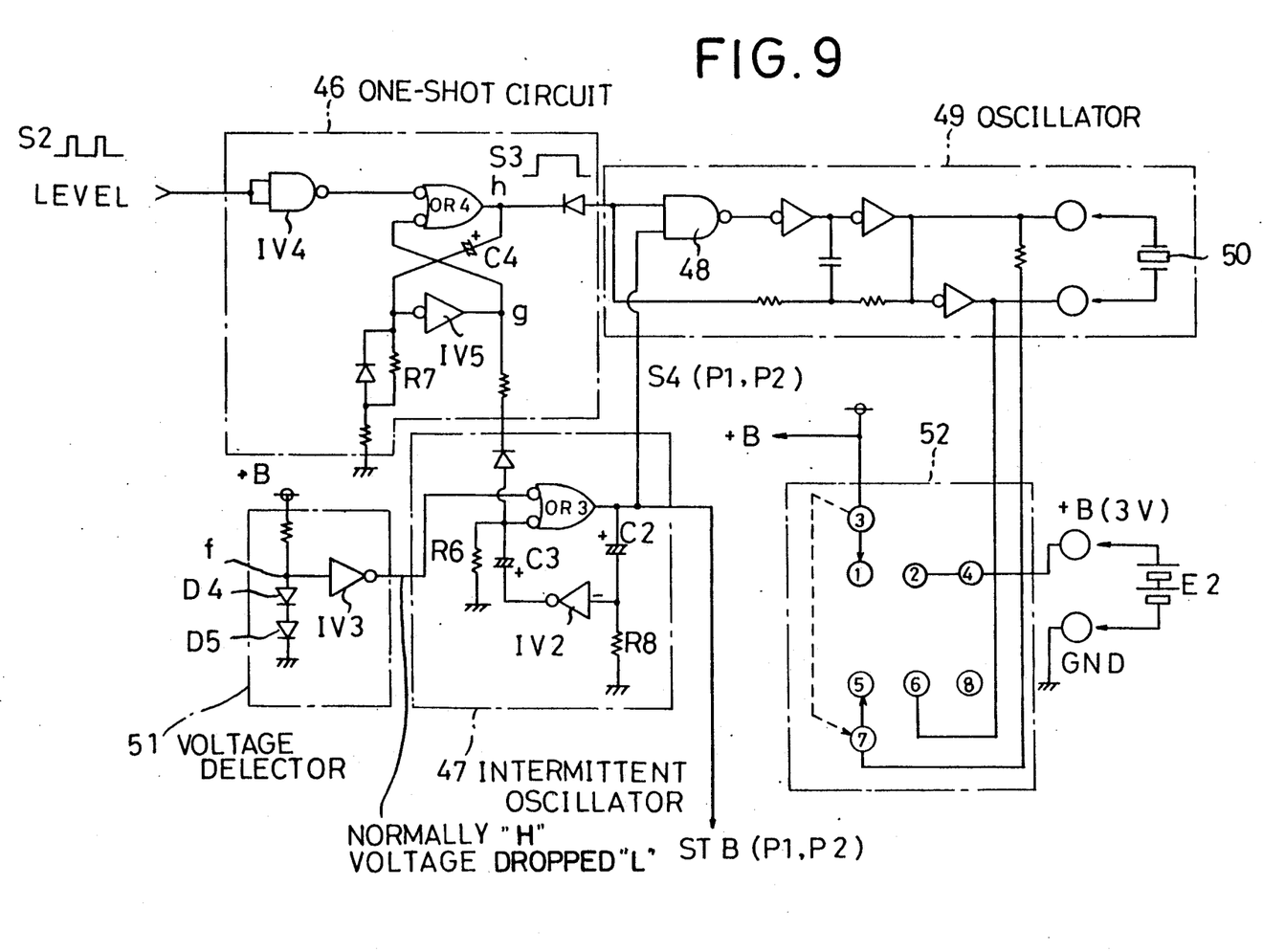

FIG. 7 shows a concrete example of the RF signal transmitter circuit and FIGS. 8 and 9 show concrete examples of the RF signal receiver, respectively.

The RF signal transmitter shown in FIG. 7 comprises an oscillator circuit 34, an amplifier circuit 35, a one-shot circuit 36 and a voltage detector circuit 37 and is adapted to be driven by a source battery E1 having a source voltage +B (e.g., 3 V). A frequency generated by a quartz oscillator 38 of the oscillator circuit 34 is amplified by the amplifier 35 and transmitted through the antenna 9. The oscillator portion 10 corresponds to a combination of the oscillator circuit 34 and the amplifier 35. The one-shot circuit 36 and the voltage detector 37 are new components and operations thereof will be described in detail later. Bases of a transistor TR1 of the oscillator 34 and a transistor TR2 of the amplifier 35 are connected to an output of the one-shot circuit 36.

RF signal receivers shown in FIGS. 8 and 9 are driven by battery E2 (FIG. 9) having source voltage +B (e.g. 3 V), respectively. The receiver in FIG. 8 comprises a tuning circuit 41, a high frequency amplifier 60, a frequency onverter 42, an intermediate frequency (IF) amplifier 43, a filter 44 and a detector 45 and the receiver in FIG. 9 further includes the one-shot circuit 46 and the oscillator 49. An audible signal is generated by a piezo buzzer 50 provided in the oscillator 49. An antenna 11 is the same as that shown by 9 in FIG. 4. The detector portion 13 in FIG. 4 corresponds to a combination of the tuning circuit 41, the high frequency amplifier 60, the frequency converter 42, the IF amplifier 43, the filter 44 and the detector 45. The level discriminator 15 in FIG. 4 corresponds to the one-shot circuit 46. The signal generator 5 and the loud speaker 6 in FIG. 4 correspond to the oscillator 49 and the piezo buzzer 50.

As shown in FIG. 9, a voltage detector 51 and an intermittent oscillator 47 are provided in each of the RF signal receiver, which will be described in detail later. Outputs of the one-shot circuit 46 and the intermittent oscillator 47 are connected to inputs of an AND gate 48 of the oscillator 49.

Figure 10:
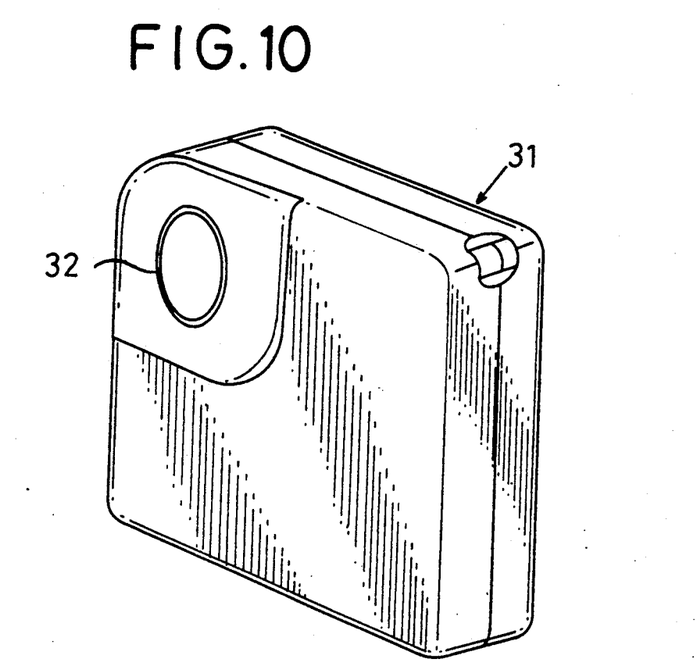
FIG. 10 is a perspective view of another example of the portable unit.

The RF signal generator shown in FIG. 7 is mounted in the portable unit 31, as shown in FIG. 10. A push-button 32 in FIG. 10 is identical to that shown by the same reference neumeral in FIG. 7.

Figure 11:
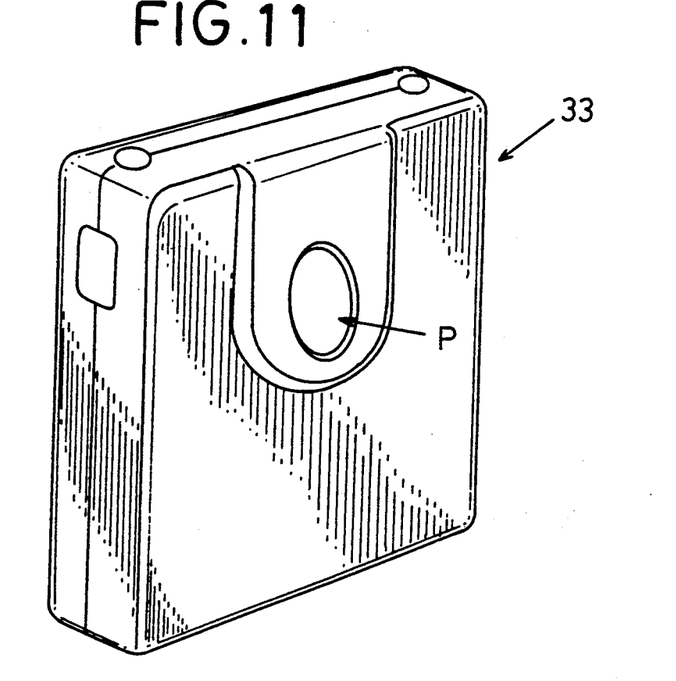
FIG. 11 is a perspective view of another example of the position indicator unit.

Either of the RF signal generators shown in FIGS. 8 and 9 is mounted on the position indicator unit 33, as shown in FIG. 11. the piezo buzzer 50 in FIG. 9 is arranged in a position P.

When a visually handicapped person carrying the portable unit 31 depresses the button 32, the buzzer 50 of the position indicator unit 33 generates sound to guide him to the place where the latter is disposed.

In a case when either or both of the batteries E1 (FIG. 7) of the portable unit 31 and E2 (FIG. 9) of the position indicator unit 33 are discharged to a level at or under which the signal transmission and/or receiving becomes impossible, it is detected by an operation of the combined one-shot circuit 36 and the voltage detector 37 in FIG. 7 or the combined voltage detector 51 and the intermittent oscillator 47 in FIG. 9.

In FIG. 7, the one-shot circuit 36 comprises a pair of OR gates OR2 and OR2, resisters R1, R2 and R3 and a capacitor C1. An output of the OR gate OR1 is connected to the aforementioned transisters TR1 and TR2, the resister R1 being connected to an output of an inverter IV1 of the voltage detector 37 through a diode D1. The inverter IV1 may be of CMOS type in which an inversion level is changed according to the level of the battery voltage +B. A fraction of the battery voltage +B obtained by series connected diodes D2 and D3 is applied to an input of the inverter IV1. Since a diode has a general tendency of holding a substantially constant voltage across it terminals regardless of current flowing therethrough, a voltage Vab between points a and b is maintained at a substantially constant value. In this embodiment, each of the diodes D2 and D3 has a voltage characteristics of 0.6 V in view of the battery voltage of 3 V. That is, Vab is set to substantially 1.2 V.

When the battery E1 is maintained 3 V, the output of the inverter IV1 is in "L" state.

In this normal state, when the switch 32 is depressed to turn it on, a "L" level is applied temporarily (time being variable by a time for which the switch 32 is depressed) to one (C) of the terminals of the OR gate OR1, by which the capacitor C1 is charged and then discharged through the resisters R1 and R2 because the output of the inverter IV1 is in "L" level. The output levels of the OR gates OR1 and OR2 are kept in "H" and "L" states, respectively, during the terminal voltage of the capacitor C1 is higher than the inversion level Vr of the OR gate OR2.

Figure 14:
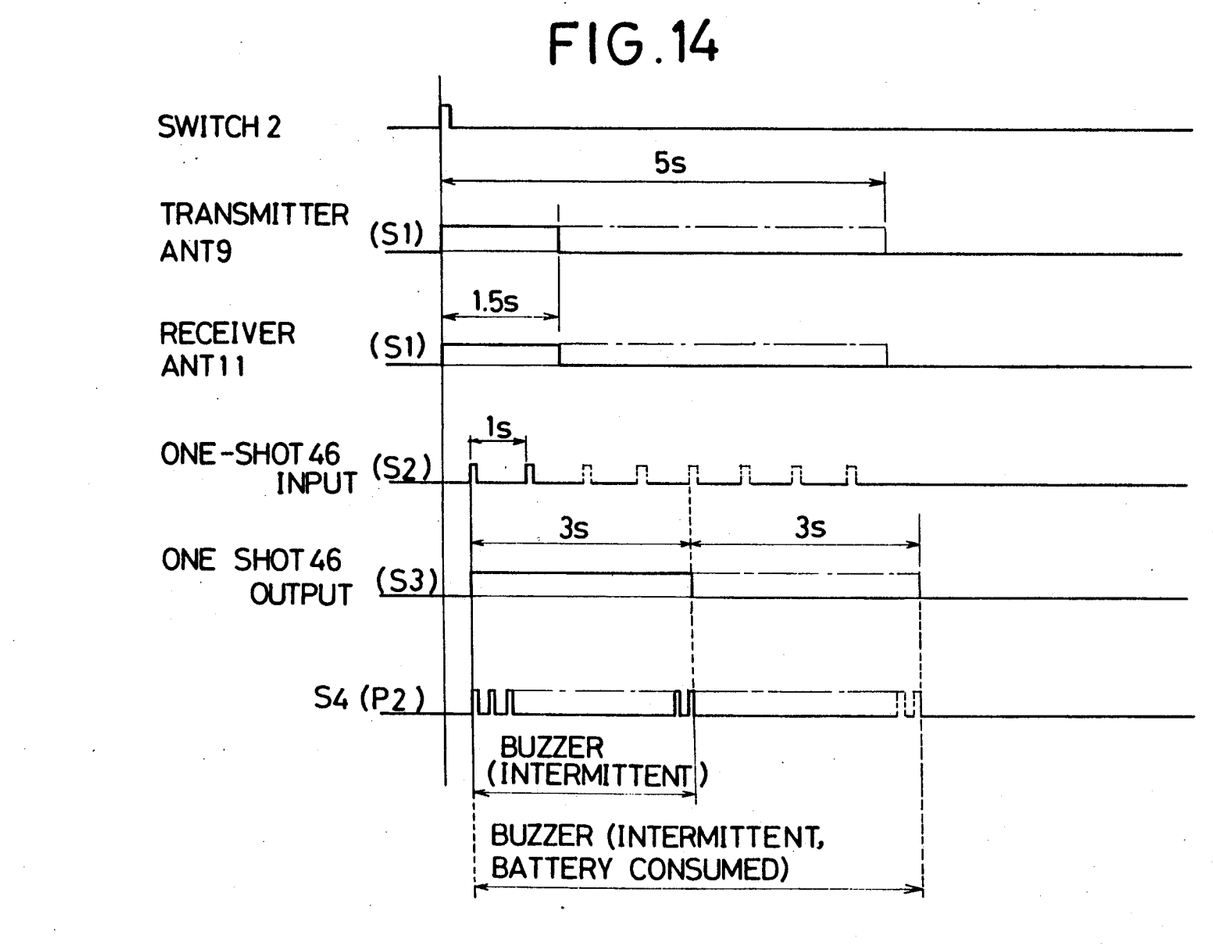

In this embodiment, constants of the respective circuit elements are selected such that a time for which the output of OR gate OR1 is in "H" level is about 1.5 seconds. For the latter time, the one-shot circuit 36 outputs "H" level and, therefore, the oscillator 34 and the amplifier 35 are energized to transmit a signal S1 through the antenna 9. Thus, the signal S1 is transmitted for about 1.5 seconds (FIG. 14).

In FIG. 9, the intermittent oscillator 47 includes an OR gate OR3 and an inverter IV2. To one of inputs of the OR gate OR3, a voltage detector 51 is connected. The voltage detector 51 includes, as in the voltage detector 37 of the transmitter (FIG. 7), an inverter IV3 and diodes D4 and D5. The inverter IV3 is also of the type whose inversion level is varied according to the source voltage +B. Since the source voltage +B is about 3 V, the diodes D4 and D5 are selected such that a voltage Vf across the diodes becomes about 1.2 V.

When the voltage +B of the battery E2 is normal and kept at about 3 V, an output level of the inverter IV3 is "H".

In this normal condition, when a receiving signal S2 is not input to the one-shot circuit 46, i.e., the antenna 11

(FIG. 8) is not receiving a receiving signal S1, a level at an output g of the inverter IV5 is "H". In such condition, a pulse signal P1 shown by (a) in FIG. 13 appears at the output of the OR gate OR3 due to self-oscillation. In this case, a pulse width Ta depends on a capacitance of the capacitor C2 and a resistance of a resister R8, which is, in this embodiment, in the order of 0.15 seconds. Further, a pulse width Tb depends, mainly on a capacitance of the capacitor C3 and a resistance of a resistor R6, which is, in this embodiment, set to about 1 second.

The pulse signal from the OR gate OR3 is fed to an AND gate 48 as a signal S4 and to bases of respective transistors of the frequency converter 42, the IF amplifier 43 and the detector 45 as a STB signal (strove signal), as shown in FIG. 8.

Since there is no signal S2 inputted to the one-shot circuit 46, the output level of the latter to the AND gate 48 is "L" and the oscillator 49 does not oscillate. Therefore, the buzzer 50 of the oscillator 49 does not produce sound even if an intermittent pulse P1 (S4) from the intermittent oscillator 47 is supplied to the AND gate 48.

When the intermittent pulse signal P1 is fed to the respective circuits of the receiver (FIG. 8) as the STB signal, these circuits operate for a rising time of the pulse, i.e., Ta=0.15 seconds. The intermittent periodical driving of the receiver is to avoid a rapid consumption of the battery E2.

Figure 13A:
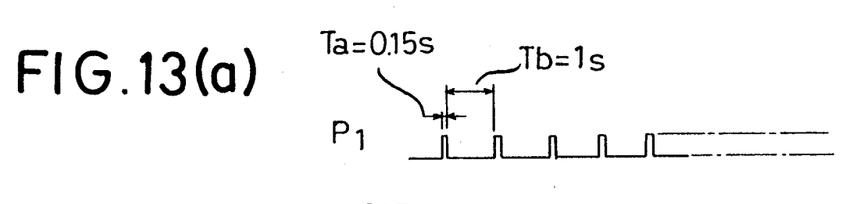

When the signal S1 transmitted from the transmitter (FIG. 7) is received by the antenna 11 of the receiver (FIG. 8), it is processed by the tuning circuit 41, the high frequency amplifier 60, the frequency converter 42, the IF amplifier 43, the filter 44 and the detector 45. The construction of the receiver mentioned above is the so-called super heterodyne receiver. In this case, the frequency converter 42 and other circuits operate in synchronism with the pulse signal P1 (FIG. 13a). Therefore, the signal S2 from the detector 45 takes in the form of narrow pulse as shown in FIG. 14. In this embodiment, the output signal S2 includes two pulses at most (FIG. 14) because the pulse width of the signal S1 is about 1.5 seconds and the pulse signal P1 (FIG. 13a) inputted as the STB signal has a period of about 1 second.

Figure 13B:
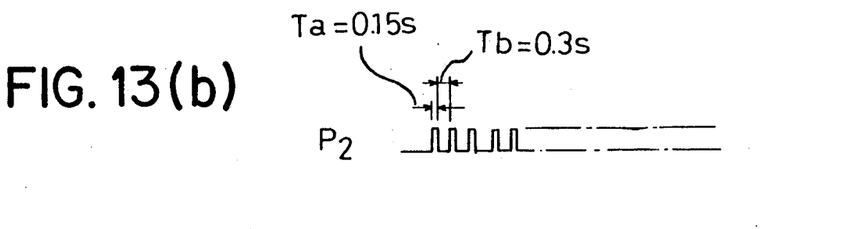

The output signal S2 is then fed to the one-shot circuit 46 in FIG. 9 and inverted by the inverter IV4. The inverted signal is supplied to one of the inputs of the OR gate OR4. When a pulse of the signal S2 is supplied to the OR gate OR4, a signal S3 which is in "H" state for a time determined by a time constant of a capacitor C4 and a resister R7, say, 3 seconds, is obtained at a point h. The point g a potential at which has been "H" is becomes "L" at that time, which is held for the same time. Therefore, the discharge time of the capacitor C3 of the intermittent oscillator 47 is shortened, resulting in the self-oscillation pulse period shortened, as shown in FIG. 13b. In this embodiment, it is shortened from about 1 second to about 0.3 seconds. Therefore, during the signal S3 is provided by the one-short circuit 46, a pulse signal P2 having shorter period is applied to the other input of the AND gate 48, as shown in FIG. 14. As a result, the buzzer 50 produces an intermittent sound of periodicity of about 0.45 seconds for about 3 seconds, which is used to guide a visually handicapped person.

A switch 52 shown in FIG. 9 functions as a power switch as well as sound volume switch. That is, when it connects terminals 1 and 5, the power is turned off, terminals 2 and 6, sound level becomes low and terminals 4 and 8, the level becomes high.

The operation of the portable unit 31 and the position indicator 33 in normal use has been described.

Now, a case where the battery E1 (FIG. 7) of the portable unit 31 or the battery E2 (FIG. 9) of the position indicator unit 33 is discharged will be described.

BATTERY E2 CONSUMMED

Since the portable unit 31 is normal, the signal S1 is transmitted through the antenna 9 (FIG. 7) when the switch 32 is closed. The signal S1 is received by the antenna 11 (FIG. 8) and the signal S2 is inputted to the one-shot circuit 46 (FIG. 9), as mentioned previously.

Figure 15:
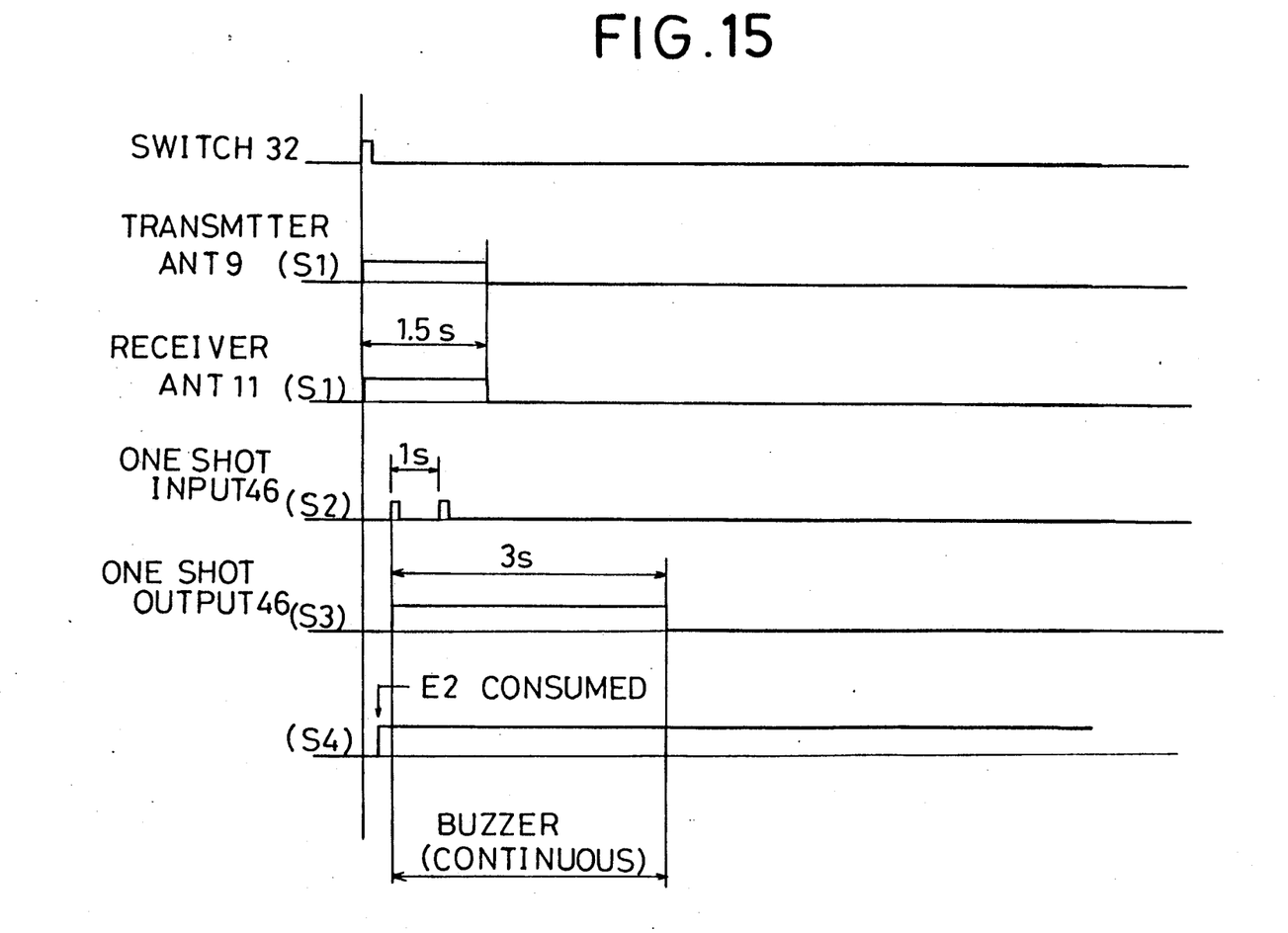

In FIG. 9, with the battery E2 consumed, the voltage level applied to the inverter IV3 is lowered. As mentioned previously, the inversion level of the inverter IV3 is changed by change of the applied voltage. Assuming that the voltage level is lowered from 3 V to 2 V, the inversion level is lowered from 1.5 V to 1 V. In this case, the input voltage Vf is always kept at the constant value, say, 1.2 V, by the diodes D4 and D5 regardless of the inversion level change. Therefore, the output of the inverter IV3 is changed from "H" in the normal state to "L" and, thus, the OR gate OR3 provides its output "H" which is supplied to the AND gate 48 as a signal S4 (FIG. 15). As a result, the buzzer 50 produces sound continuously for a time during which an OR gate OR4 of the one-shot circuit 46 is "H", i.e., about 3 seconds, indicating a consumption of the battery E2 of the position indication unit 33.

BATTERY E1 CONSUMMED

When the battery E1 of the portable unit 31 is consummed, the voltage applied to the inverter IV1 of the voltage detector 37 in FIG. 7 is lowered, upon which the output of the inverter IV1 is changed from "L" to "H" as for the same reason for the voltage detector 51 (FIG. 9).

Figure 12:
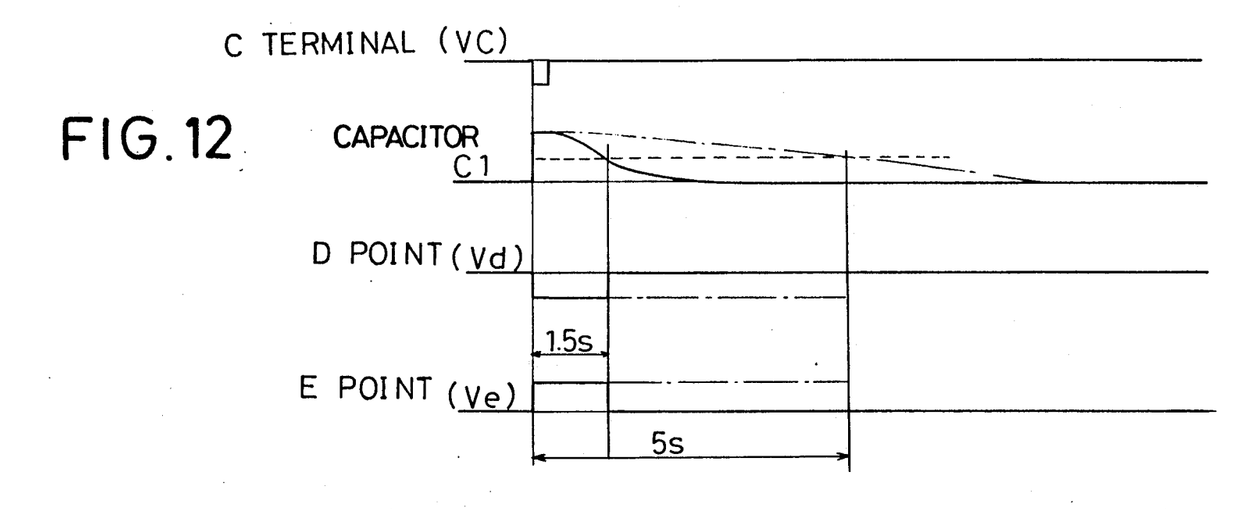
FIGS. 12 to 15 show timing charts of operations of the circuits shown in FIGS. 7 to 9, respectively.

With the output "H" of the inverter IV1, the discharge current of the capacitor C1 of the one-shot circuit 36 flows through not the resister R1 but the resister R2. As a result, the discharge time of the capacitor C1 is longthened, so that the potential at an output point e of the OR gate OR1 is kept at "H" for a long time, say, about 5 seconds, as shown by a chain line in FIG. 12. Therefore, the signal S1 is transmitted from the antenna 9 for about 5 seconds as shown by a chain line in FIG. 14, which is received by the antenna 11.

In the receiver (FIG. 8), the signal S2 including pulses corresponding, in number, to the period of the signal S1 (about 5 seconds) is produced, which is supplied to the one-shot circuit 46 (FIG. 9).

The output signal S3 of the OR gate OR4 of the one-shot circuit 46 is "H" for about 3 seconds in the normal state (FIG. 14). However, when the battery E1 as consummed, the signal S2 is supplied to the circuit 46 continuously even after the period of about 3 seconds lapses. Therefore, a second S3 signal is produced continuously to the first S3 signal, resulting in that the AND gate 48 is opened continuously for totally about 6 seconds. Therefore, the buzzer 50 is operated intermittently with a period of about 6 seconds, indicating the consumption of the battery E1.

When both of the batteries E1 and E2 of the portable unit 31 and the position indicator unit 33 are consummed, the position indicator unit produces the continuous sound with the period of about 6 seconds similarly.

What is claimed is:

1. A guide system for visually handicapped persons, comprising at least one portable unit including a battery voltage detector circuit, a radio frequency signal oscillator, means for transmitting radio frequency oscillations from said oscillator, and a transmitting time control circuit for controlling said transmitting means to transmit said signals for a first predetermined time duration, said portable unit being adapted to be carried by a visually handicapped person, and a position indicator unit including a battery voltage detector circuit, a radio frequency signal receiver for receiving radio frequency oscillations transmitted by said portable unit, a loudspeaker, a loudspeaker actuating circuit for actuating said loud speaker in response to the reception of signals from said portable unit, and a loudspeaker duration control circuit for controlling the duration of actuation of said loudspeaker by said actuating circuit, said position indicator unit being adapted to be located at a position to which the visually handicapped person is to be guided, and source batteries included in said portable unit and said position indicator unit, said transmitting time control circuit being responsive to detection of lowering of the battery voltage of the portable unit by the battery voltage detector therein, to change the actuating time of said transmitting means to a second predetermined time duration different from said first duration, said loudspeaker duration control circuit being responsive to reception by said position indicator unit of signals transmitted by said transmitting means for said first and second durations to control said actuating circuit to actuate said loudspeaker for third and fourth different durations, respectively, said loudspeaker duration control circuit being responsive to detection of lowering of the battery voltage of the position indicator unit by the battery voltage detector circuit in the position indicator unit to control said actuating circuit to actuate said loudspeaker for a fifth time duration different from said third and fourth duration, in response to reception of signals of said first duration.

2. The guide system of claim 1, wherein said, loudspeaker duration control circuit is responsive to the detection of lowering of the battery voltage of the position indicator unit by the battery voltage detector therein to control the loudspeaker actuating circuit to actuate the loudspeaker for a time duration different from said third and fourth durations.

3. A guide system comprising at least one portable unit including a battery voltage detector circuit, means for transmitting radio frequency signals, and a transmitting time control circuit for controlling said transmitting means to transmit said signals for a first predetermined time duration, and a position indicator unit including a battery voltage detector circuit, a radio frequency signal receiver for receiving radio frequency signals transmitted by said portable unit, a loudspeaker, means for energizing said loud speaker in response to the reception of said signals transmitted from said portable unit, said means for energizing said loudspeaker comprising a loudspeaker duration control means for controlling the duration of energization of said loudspeaker by said energizing means, and source batteries included in said portable unit and said position indicator unit, said transmitting time control circuit comprising means responsive to detection of lowering of the battery voltage of the portable unit by the battery voltage detector therein, to change the energizing time of said transmitting means to a second predetermined time duration different from said first duration, said loudspeaker duration control means comprising means responsive to reception by said position indicator unit of signals transmitted by said transmitting means for said first and second durations to control said energizing means to energize said loudspeaker for third and fourth different durations, respectively, said loudspeaker duration control means being responsive to detection of lowering of the battery voltage of the position indicator unit by the battery voltage detector circuit therein to control said energizing means to energize said loudspeaker for a fifth time duration different from said third and fourth duration, in response to reception of said signals from said transmitting means.

* * * * *